United States Patent [19]

Steffee

[11] Patent Number: 4,790,303
[45] Date of Patent: Dec. 13, 1988

[54] APPARATUS AND METHOD FOR SECURING BONE GRAFT

[75] Inventor: Arthur D. Steffee, Moreland Hills, Ohio

[73] Assignee: AcroMed Corporation, Cleveland, Ohio

[21] Appl. No.: 24,577

[22] Filed: Mar. 11, 1987

[51] Int. Cl.$^4$ ............................................... A61F 5/04
[52] U.S. Cl. ............................. 128/924 M; 128/924 J; 128/924 C
[58] Field of Search .......... 128/92 YF, 92 YC, 92 YJ, 128/92 YM, 92 YD, 92 YE

[56] References Cited

U.S. PATENT DOCUMENTS

| | | | |
|---|---|---|---|
| 4,047,523 | 9/1977 | Hall | 128/924 M X |
| 4,135,506 | 1/1979 | Ulrich | 128/92 Y R |
| 4,369,770 | 1/1983 | Bacal et al. | 128/924 M X |
| 4,404,967 | 9/1983 | Bacal et al. | 128/924 M X |
| 4,438,769 | 3/1984 | Pratt et al. | 128/92 YC |
| 4,454,875 | 6/1984 | Pratt et al. | 128/92 YC |
| 4,462,395 | 7/1984 | Johnson | 128/92 YC |
| 4,503,847 | 3/1985 | Mouradian | 128/92 YZ |
| 4,570,618 | 2/1986 | Wu | 128/924 J X |
| 4,570,623 | 2/1986 | Ellison et al. | 128/92 YC |

FOREIGN PATENT DOCUMENTS 2649042  9/1978  Fed. Rep. of Germany ... 128/924 M

OTHER PUBLICATIONS

Journal of Bone & Joint Surg., vol. 38-A#5, Oct. 1956, pp. 1156-1158, "Boat-Nail Fixation of Tendon & Ligaments to Cancellous Bone", by Lt. Col. R. W. Augustine et al.

Primary Examiner—Robert A. Hafer
Assistant Examiner—Kevin G. Rooney
Attorney, Agent, or Firm—Tarolli, Sundheim & Covell

[57] ABSTRACT

A fastener for securing bone graft between a pair of bone portions. The fastener includes a curved elongated member having a shank for extending into the bone graft and pair of bone portions. The shank has an end portion which receives a force for driving the shank into the pair of bone portions and the bone graft. The shank has a plurality barbs projecting therefrom for resisting movement of the shank relative to the bone graft and the bone portions.

8 Claims, 5 Drawing Sheets

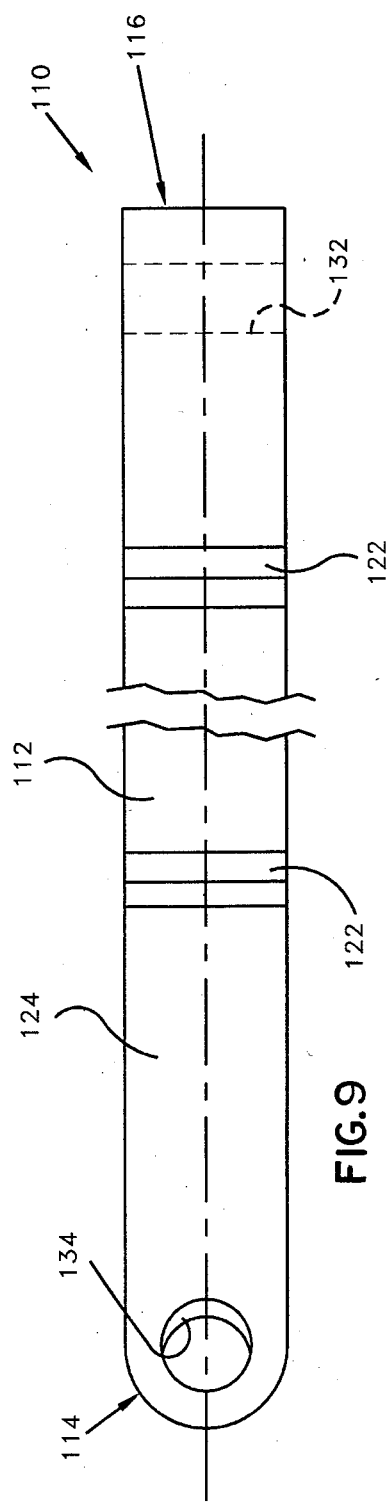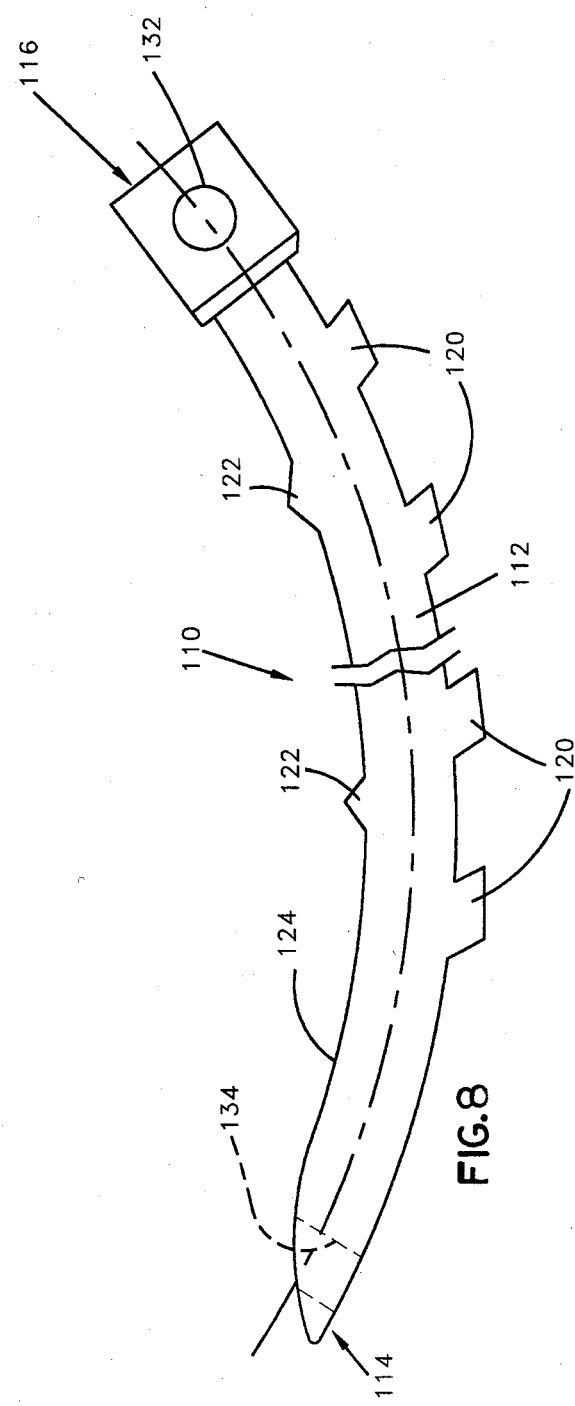

APPARATUS AND METHOD FOR SECURING BONE GRAFT

BACKGROUND OF THE INVENTION

The present invention relates to securing bone graft between a pair of bone portions, and in particular, relates to a fastener for securing bone graft between a pair of bone portions.

It is known that bone graft contracts as it resorbs. This characteristic of bone graft has resulted in difficulties in securing bone graft between spaced apart bone portions which are to be connected by the bone graft. Typically, staples are used to secure bone graft between bone portions. As the bone graft resorbs, it applies a force to a leg of the staple. The force acts through a moment arm and causes the leg to pivot relative to a portion of the staple base. This causes the staple to loose its effectiveness.

SUMMARY OF THE PRESENT INVENTION

The present invention is directed to a fastener for securing bone graft between a pair of bone portion. The fastener embodying the present invention comprises a curved elongated member having a shank for extending into the bone graft and the pair of bone portions to secure the bone graft and pair of bone portions together. The shank extends through the bone graft in a direction along a line extending through the bone graft and bone portions and along which the bone graft resorbs. Thus, the force applied to the shank by the bone graft as it resorbs acts generally along the longitudinal extent of the shank. Thus, the force does not act through a moment arm nor does it have a detrimental effect on the fastener.

The shank has an end portion for receiving force for driving the shank into the pair of bone portions and the bone graft. Since the shank is curved, it may be driven into one bone portion through a surface thereof which may extend transversely relative to a surface of the bone graft through which the shank will extend. As it progresses through the bone portion it moves in a curved path into the bone graft and then into the other bone portion. The shank has barbs extending therefrom to resist movement of the shank relative to the bone graft and the bone portions once it has been driven into place.

The shank also has an opening extending through the end portion for receiving a member such as a wire. Thus, it is possible to secure the bone graft and bone portions with two fasteners one of which is driven into the bone portions and bone graft in one direction and the other of which is driven into the bone portions and bone graft in the opposite direction. The wire can interconnect the opposite end portion of the respective fasteners and assist in retaining the fasteners in position. Specifically, if one of the fasteners tends to move out of the bone portions in a direction, opposite the direction in which it was driven, it would be resisted by the other fastener which would have to move in the same direction it was driven and further into the bone portions.

DESCRIPTION OF THE DRAWINGS

Further features and advantages of the present invention will be apparent to those skilled in the art to which it relates from reading the following detailed description of a preferred embodiment thereof with reference to the accompanying drawings, in which:

FIG. 8 is a side elevational view of a fastener of another embodiment of the present invention; and FIG. 9 is a top plan view of the fastener of FIG. 8 looking at the fastener in the direction of line 9—9.

DESCRIPTION OF A PREFERRED EMBODIMENT

It is well known that bone graft when located between a pair of bone portions contracts as it resorbs. This creates problems in securing the bone graft in position between the bone portions. A variety of different techniques have been utilized to secure bone graft between bone portions. The present invention is directed to a simple yet extremely effective fastener for securing bone graft in position between a pair of bone portions to be interconnected by the bone graft.

Figure 1:
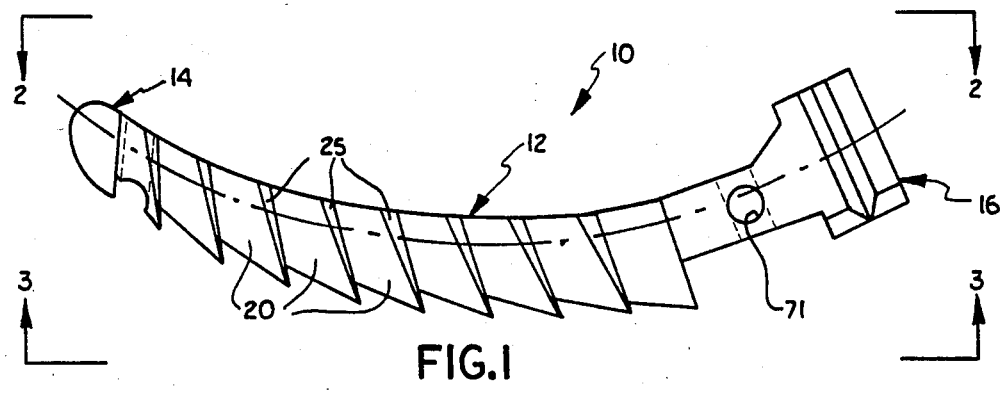
FIG. 1 is a side elevational view of a fastener embodying the present invention.
Figure 2:
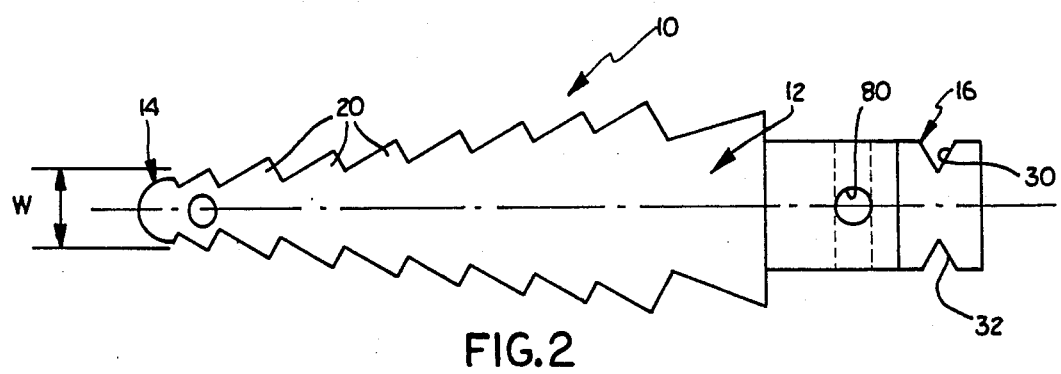
FIG. 2 is a top plan view of the fastener of FIG. 1 looking at the fastener in the direction of line 2—2.
Figure 3:
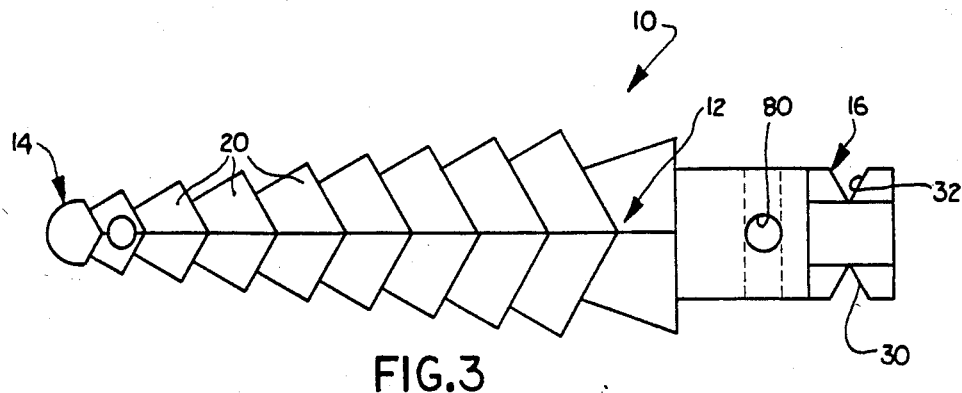
FIG. 3 is a bottom plan view of the fastener of FIG. 1 looking at the fastener in FIG. 1 in the direction of the arrow 3—3 in FIG. 1.

An elongated curved fastener 10 embodying the present invention is illustrated in FIGS. 1-3. The fastener 10 includes a shank portion 12. The shank portion 12 has a pointed end 14 and at its opposite end has a driving head portion 16. A plurality of barbs 20 are spaced along the shank portion 12 and project therefrom.

The fastener 10 is preferably made from a metal material which is compatible with human tissue. Such a metal material may be titanium or surgical grade stainless steel.

Figure 5:
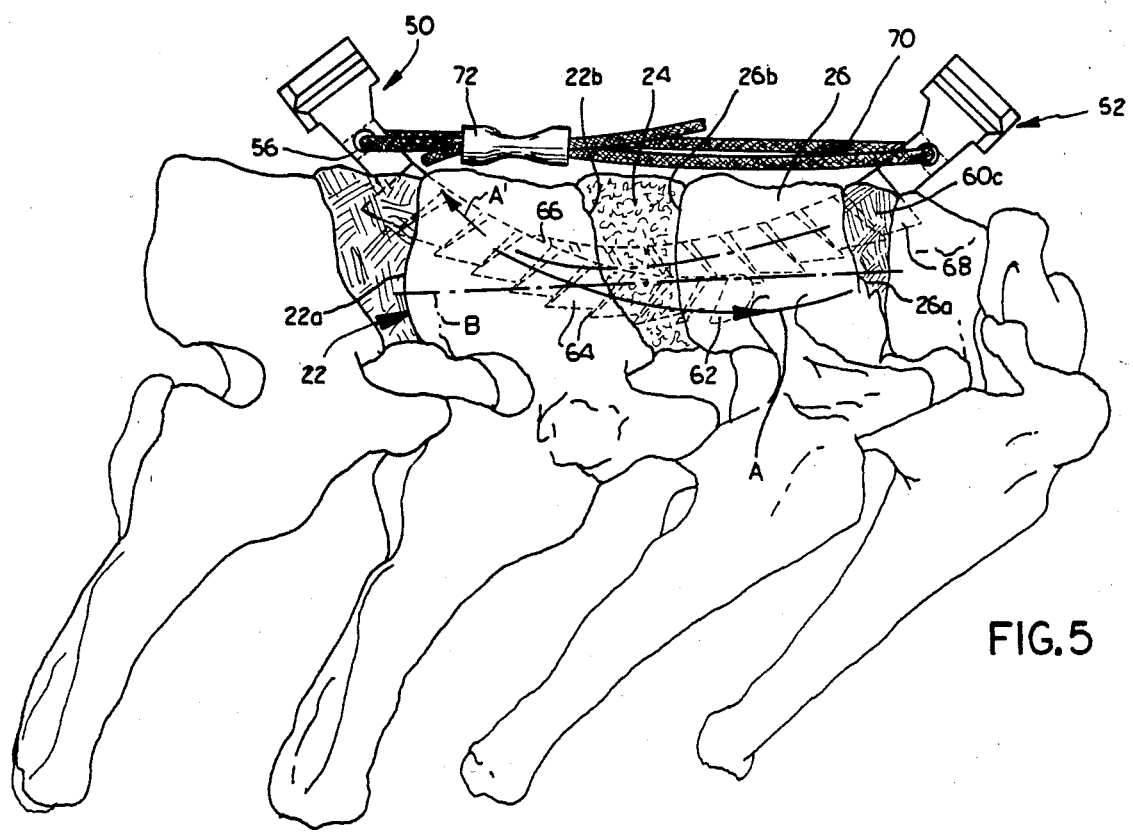
FIG. 5 is a side view of the fasteners securing the bone graft between the bone portions.

The pointed end 14 of the fastener 10 is placed in contact with a surface 22a of a bone portion 22 (FIG. 5). The fastener 10 is driven into the bone portion 22. As the fastener 10 is driven into the bone portion, due to its curved configuration, it progresses along a curved path A through the bone graft 24 and into bone portion 26. The part of the shank portion 12 which extends through the bone graft 24 lies along a line B which extends generally in the direction in which the bone graft resorbs. Thus, the bone graft 24, as it resorbs, applies a force on the shank portion 12 which acts generally along the path A of the shank portion 12.

Each of the barbs 20 on the shank portion 12 have a width W (FIG. 2) which progressively increases as the barbs 20 extend in a direction along the path A opposite the direction in which the fastener is driven. Thus, the fastener 10 appears to be tapered, as viewed in FIGS. 2 and 3, from its end portion 14 and increases in width to the end portion 16 of the shank portion 12. Also, the barbs 20 have surfaces 25 which are inclined rearwardly. The surfaces 25 extend in a direction forming an acute angle with the path A along which the fastener is driven. The surfaces 25 are inclined to resist withdrawal of the fastener 10 from the bone portions 22, 36 and the bone graft 24 in a direction opposite the path A along which the fastener is driven.

Figure 7:
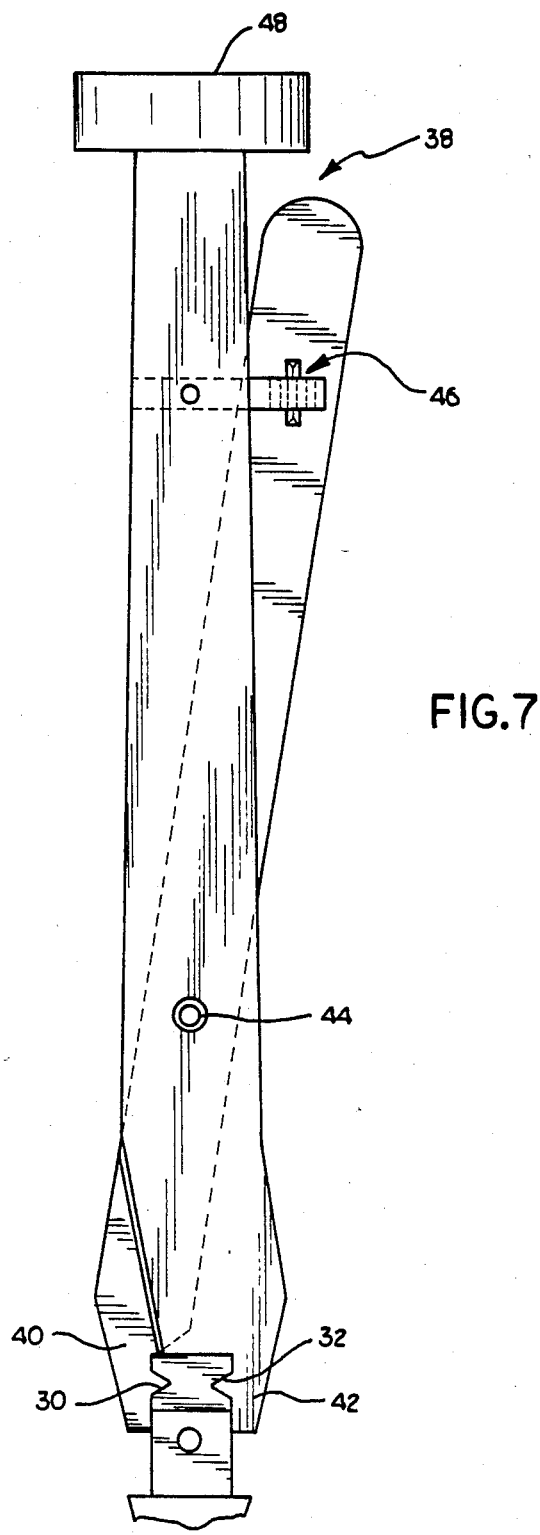
FIG. 7 is a schematic view of a tool used for holding and driving the fastener of the present invention.

The end 16 of the shank portion of the fastener includes a pair of opposite V-shaped grooves 30, 32. The grooves 30, 32 are adapted to receive gripping jaws 40, 42 respectively, of a driving tool 38 (FIG. 7). The tool 38 holds and drives the fastener 10 into the bone portions 22, 26 and bone graft 24. The tool 38 includes the gripping jaws 40, 42, which are pivotally attached at pivot 44. A ratchet locking mechanism 46 locks the jaws 40, 42 in the grooves 30, 32. The fastener 10 is thus gripped in the jaws 40, 42. The driving tool 43 further includes a surface 48 which may be struck with a hammer to drive the fastener 10 into the bone portions 22, 26 and the bone graft 24.

Figure 4:
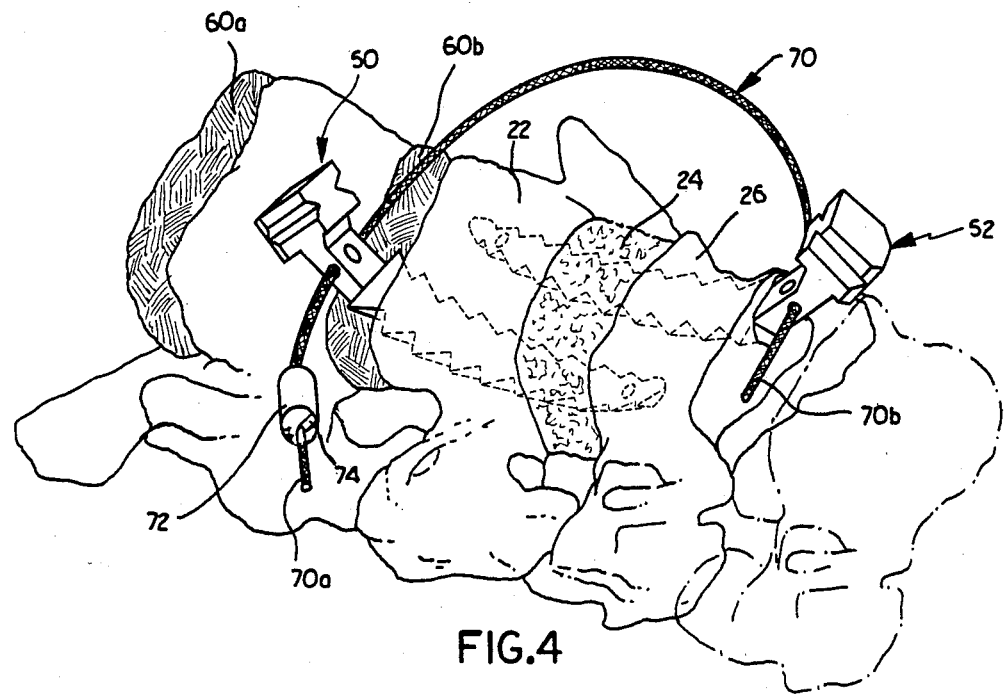
FIG. 4 is a view illustrating fasteners embodying the present invention interconnecting a bone graft between a pair of bone portions.

The manner and the various locations in the body in which a fastener embodying the present invention may be utilized are numerous. FIGS. 4 and 5 show one specific arrangement in which a pair of fasteners 50, 52 embodying the present invention are driven into bone portions 22, 26 and bone graft 24 located therebetween. The procedure of which is described below.

The fastener 50 is inserted between the fibrocartilaginous disk 60b and surface 22a of bone portion 22. The pointed end portion 62 of the fastener 50 is driven through the surface 22a of the bone portion 22 by a driving force transmitted through a suitable tool, such as the driving tool 38 (FIG. 7). The pointed end portion 62 of the fastener 50 is driven through the bone portion 22 and exits the bone portion through surface 22b. The surface 22b of the bone portion extends in substantially the same direction as surface 22a. The pointed end portion 62 of the fastener 50 is then driven through the entire thickness of the bone graft 24 and into the bone portion 26 through surface 26b. The pointed end portion 62 of the fastener 50 is stopped within the bone portion 26. The barbs 64 of the fastener 50 resist movement of the fastener in a direction along the path A opposite to the direction in which the fastener was driven.

The end portion 66 of the fastener 52 is similarly driven in a direction opposite the direction in which fastener 50 was driven. The fastener 52 is spaced laterally from fastener 50 in the bone portions and extends completely through the bone portion 26 between surfaces 26a and 26b and the bone graft 24. The end portion 66 of the fastener 52 is stopped within the bone portion 22. The barbs 68 of the fastener 52 resist movement in a direction opposite the direction in which the fastener 52 was driven.

After the fasteners 50, 52 have been driven into the bone portions 22, 26 and the bone graft 24 a wire cable 70 is placed through openings 71 in the driving ends of the respective fasteners 50, 52. The wire cable 70 is made from a material compatible with human tissue, such as braided surgical grade stainless steel fibers. The ends 70a, 70b of wire cable 70 are secured together by a suitable connector 72.

The connector 72 is made of a material which can be deformed or crimped to frictionally engage the ends 70a, 70b of the wire cable 70 and maintain the ends of the wire cable 70 in a desired position relative to one another. The connector 72 has a portion 74 which is split extending longitudinally of the length of the connector. The ends 70a, 70b are placed within the split portion 74 in the desired relative position. The connector is then deformed or crimped by a suitable tool to maintain the wire cable in a desired tension.

The fastener 50 is driven into the bone portions 22, 26 and bone graft 24 in the direction A. The fastener 52 is driven into the bone portions 22, 26 and the bone graft 24 in the direction A'. If the fastener 50 tends to withdraw from the bone portions 22, 26 and bone graft 24 in a direction opposite the direction in which it was driven, it would tend to pull the fastener 52 further into the bone portions 22, 26 due to the wire cable 70 which innerconnects the ends of the fasteners 50, 52. This obviously would occur also if the fastener 52 tended to withdraw from the bone portions 22, 26 and bone graft 24. The withdrawal of fastener 52 would be resisted by the fastener 50 and the wire cable 70 which innerconnects the fasteners. Thus, this attachment of the bone portions 22, 26 and the bone graft 24 is made extremely reliable.

Further it should be apparent that the fasteners 10 also have an opening 80 at the end 12 thereof. As a result, a wire can be inserted between the opposite ends of the fastener. Further, if desired the fastener can be used with a tapered locking pin 82 in addition to the wire cable or the tapered locking pin may be used alone to lock the fastener 10 in position. Such an embodiment is illustrated in FIG. 6.

Figure 6:
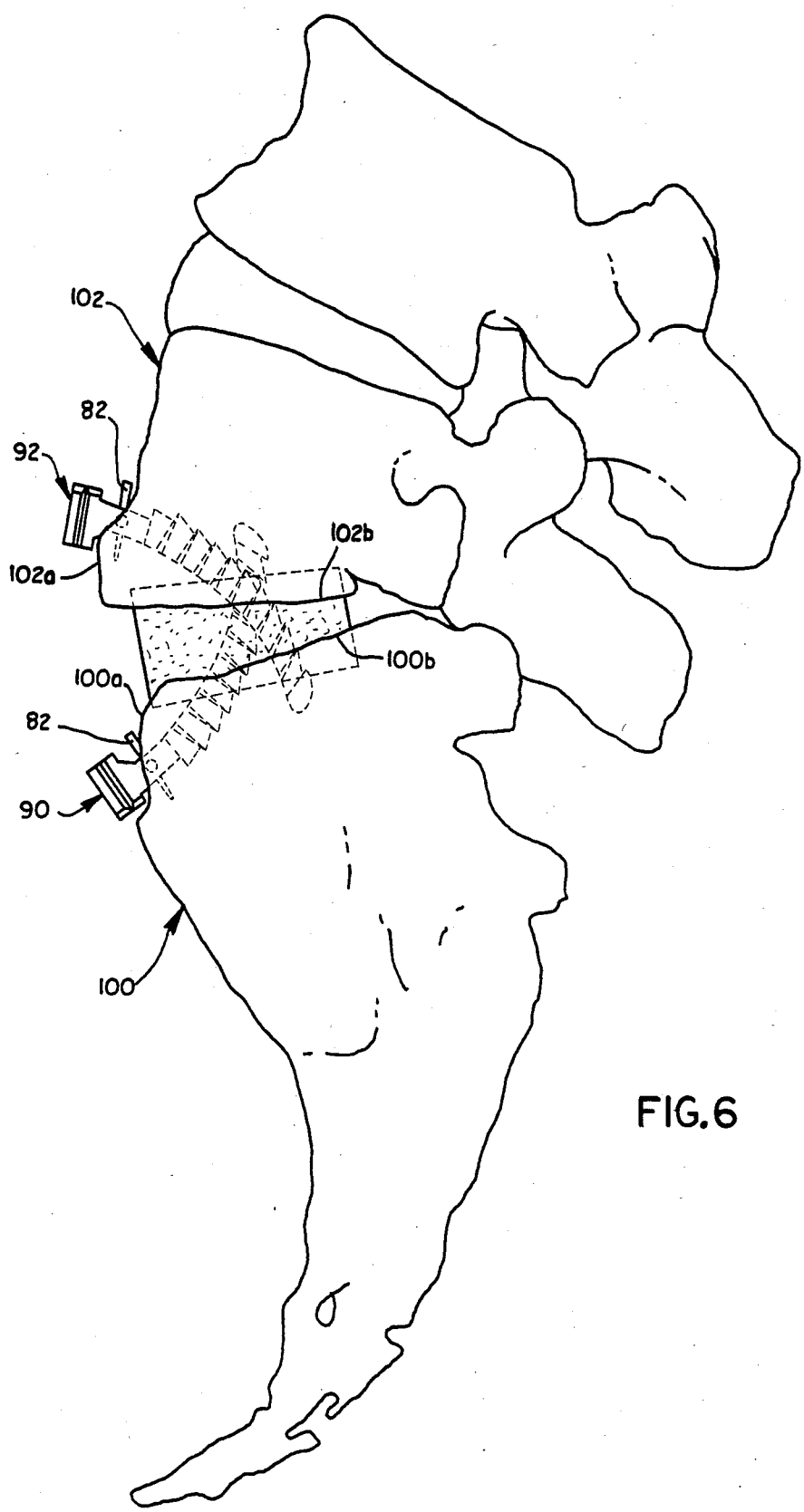
FIG. 6 is a side view of the fasteners securing the bone graft between other bone portions.

Also shown in FIG. 6 is a modified type of mounting of the fasteners. In this alternative embodiment, the fasteners 90, 92 secure the bone graft 94 between bone portions 100, 102. The fastener 90 extends through the bone portion 100 between surfaces 100a, 100b of the bone portion. The surfaces 100a, 100b of the bone portion 100 are disposed adjacent one another and extend transversely relative to one another. The fastener 92 extends through the bone portion 102 between the surfaces 102a, 102b. The surfaces 102a, 102b of the bone portion 102 are disposed adjacent one another and extend transversely relative to one another.

A fastener 110 made in accordance with a second embodiment of the present invention is illustrated in FIGS. 8 and 9. The fastener 110 is an elongate curved member having a rectangular cross section. The fastener 110 includes a shank portion 112. The shank portion 112 has a pointed leading end portion 114 and an end portion 116. The end portion 116 receives a driving force to drive the fastener 110 into a bone portion. The fastener 110 is preferably made of a metal which is compatible with human tissue. Such a metal material may be titanium or surgical grade stainless steel.

A plurality of barbs 120 extend away from a convex surface 118 of the shank portion 112 of the fastener 110. The barbs 120 are shaped to permit the fastener 110 to be easily driven into a bone portion. The shape of the barbs 120 also aids in resisting movement of the fastener 110 outwardly from the bone portion in a direction opposite the direction in which it was driven.

A plurality of ridges 122 are disposed along the concave surface 124 of the fastener 110. Each of the ridges 122 extend transversely to the longitudinal axis of the shank portion 112. The ridges 122 further aid in preventing the fastener 110 from moving relative to a bone portion. The ridges 122 extend a lesser distance away from the shank portion 112 than the barbs 120 extend.

The fastener 110 includes an opening 132 for receiving a wire therethrough to connect a pair of fasteners together, as described above. The fastener 110 also includes a second opening 134 extending through the pointed end portion 114. The opening 34 may receive a tapered pin, as described above, for further securing the fastener 110 from movement relative to a bone portion.

It should be apparent that certain modifications, changes and adaptations may be made in the present invention and it is intended to cover all such changes, modifications and adaptations which come within the scope of the appended claims.

Having described my invention, I claim:

1. A fastener for securing bone graft between a pair of bone portions, said fastener comprising:

an elongate curved member having a shank for extending into the bone graft and pair of bone portions:

said shank being a single projection with a longitudinal central axis and having a constant curvature along said longitudinal axis;

said shank having a concave surface, a convex surface and an end portion for receiving a force to drive said shank in a direction into the bone graft and pair of bone portions, said end portion being located along the longitudinal central axis of said shank; and a plurality of barbs extending from said shank and spaced along said convex surface of said shank for engaging the bone graft and pair of bone portions to resist removal of said shank from the bone graft and the pair of bone portions.

2. The fastener set forth in claim 1 wherein each of said plurality of barbs has a lesser transverse width than a preceding barb along said shank with the widest barb located adjacent said end portion for receiving a force to drive said shank.

3. The fastener set forth in claim 1 further including a plurality of transversely extending ridges spaces along said concave surface of said shank.

4. A method comprising the steps of:

placing bone graft between first and second bone portions;

providing a pair of fasteners, each of said fasteners having an elongate curved shank; said shank being a single projection with a longitudinal central axis and having a constant curvature along said longitudinal axis; and an end portion for receiving a driving force to drive the shank into the bone graft and pair of bone portions;

driving a first one of the fasteners into the first bone portion, the bone graft and then the second bone portion and driving a second one of the fasteners into the second bone portion, the bone graft and then into the first bone portion; and interconnecting the fasteners by wiring together end portions of the fasteners projecting from the bone portions.

5. An apparatus for securing bone graft between a pair of bone portions in which the bone graft contracts as it resorbs in at least one direction along a line extending between the bone portions, said apparatus comprising:

an elongate curved member having a shank for extending into the bone graft and bone portions, said shank being a single projection with a longitudinal central axis and having a constant curvature along said longitudinal axis;

an end portion on said shank for receiving a tool adapted to grip said shank and to transmit a force to drive said shank into one of the pair of bone portions, the bone graft and then the other one of the pair of bone portions; and a plurality of barbs extending from said shank in a direction allowing relative movement of one of the bone portions toward the other of the bone portions in a direction along the line extending between the bone portions as the bone graft contracts and for resisting relative movement of one of the bone portions away from the other of the bone portions in a direction along the line extending between the bone portions.

6. An apparatus for securing bone graft between a pair of bone portions, said apparatus comprising:

a pair of fasteners, each of said pair of fasteners including an elongate curved member having a shank for extending into the bone portions and the bone graft in a direction toward the other fastener, said shank being a single projection with a longitudinal central axis and having a constant curvature along said longitudinal axis; each of said pair of fasteners having a plurality of barbs extending from said shank to resist removal of said shank from the bone portions and the bone graft; and means for interconnecting said pair of fasteners to transmit a force between said pair of fasteners when one of said pair of fasteners moves in a direction tending to remove itself from the bone portions and the bone graft to thereby force the other of said pair of fasteners further into the bone portions and the bone graft.

7. The apparatus set forth in claim 6 further including an end portion on each of said pair of fasteners for extending from a respective one of the bone portions and an opening through said end portion and wherein said means for interconnecting said pair of fasteners comprises a connector having opposite end portions receivable in said respective openings in said end portion of each of said pair of fasteners.

8. The apparatus set forth in claim 7 wherein said connector comprises a wire cable extending between said end portions on each of said pair of fasteners.

* * * * *